United States Patent
Kaibel et al.

(10) Patent No.: US 7,696,360 B2
(45) Date of Patent: Apr. 13, 2010

(54) METHOD FOR THE SEPARATION OF ASCORBIC ACID FROM A POLAR SOLVENT CONTAINING ASCORBIC ACID AND 2-KETO-L-GULONIC ACID

(75) Inventors: Gerd Kaibel, Lampertheim (DE); Martin Merger, Ludwigshafen (DE); Thomas Domschke, Speyer (DE); Petra Deckert, Wiesloch (DE); Friedrich Sauer, Obersuelzen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1119 days.

(21) Appl. No.: 10/515,625

(22) PCT Filed: Jul. 7, 2003

(86) PCT No.: PCT/EP03/07256

§ 371 (c)(1),
(2), (4) Date: Dec. 6, 2004

(87) PCT Pub. No.: WO2004/007474

PCT Pub. Date: Jan. 22, 2004

(65) Prior Publication Data

US 2005/0197504 A1   Sep. 8, 2005

(30) Foreign Application Priority Data

Jul. 12, 2002   (DE) ................ 102 31 890

(51) Int. Cl.
*C07D 307/62* (2006.01)
(52) U.S. Cl. ...................................... 549/315
(58) Field of Classification Search ............ 549/315
See application file for complete search history.

(56) References Cited

U.S. PATENT DOCUMENTS

| 4,111,958 | A | * | 9/1978 | Crawford ............... 549/306 |
| 4,275,234 | A | * | 6/1981 | Baniel et al. ............ 562/584 |
| 5,041,563 | A | | 8/1991 | Fahrni et al. |
| 6,197,977 | B1 | | 3/2001 | Boettcher et al. |
| 6,610,863 | B2 | * | 8/2003 | Arumugam et al. ...... 549/315 |

FOREIGN PATENT DOCUMENTS

| CH | 187 933 | 3/1937 |
| DE | 1 904 619 | 8/1970 |
| DE | 3831071 | 3/1990 |
| EP | 0 359 645 | 3/1990 |
| EP | 0 828 725 | 3/1998 |
| GB | 1 426 018 | 2/1976 |
| JP | 53-098925 | 8/1978 |

* cited by examiner

*Primary Examiner*—Janet L. Andres
*Assistant Examiner*—Raymond Covington
(74) *Attorney, Agent, or Firm*—Oblon, Spivak, McClelland, Maier & Neustadt, P.C.

(57) ABSTRACT

The invention relates to a method for the separation of ascorbic acid from a mixture containing ascorbic acid and 2-keto-L-gulonic acid in a polar, preferably aqueous solvent, by means of liquid/liquid extraction using an amide. The method preferably also comprises steps for the back-extraction of the ascorbic acid, recycling of the extraction solvent and/or the back extraction solvent and for isolation of the ascorbic acid from the back extraction solvent. The invention further relates to a method for the production of ascorbic acid from KGA and isolation of the ascorbic acid so produced.

11 Claims, No Drawings

METHOD FOR THE SEPARATION OF ASCORBIC ACID FROM A POLAR SOLVENT CONTAINING ASCORBIC ACID AND 2-KETO-L-GULONIC ACID

CROSS REFERENCES TO RELATED APPLICATIONS

This application is a national stage application of International Patent Application No. PCT/EP03/07256, filed on Jul. 7, 2003, and claims priority to German Patent Application No. 102 31 890.5, filed on Jul. 12, 21002, both of which are incorporated herein by reference in their entireties.

L-Ascorbic acid (vitamin C, ascorbic acid, L-xyloascorbic acid, L-threo-hex-2-enonic acid γ-lactone) is conventionally prepared from 2-keto-L-gulonic acid (KGA), monoacetone-2-keto-L-gulonic acid or diacetone-ketogulonic acid. In more modern processes, KGA is produced in a single- or multistage fermentation process, for example using the two-stage fermentation of sorbitol via sorbose using microorganisms suitable for this purpose, some especially modified.

KGA and the diacetone-2-keto-L-gulonic acid produced in the "Reichstein process" are lactonized directly or via intermediates, for example esters, in particular methyl or butyl esters. The catalysts used are acids, usually mineral acids, in particular concentrated hydrochloric acid (acid lactonization) or bases, for example sodium hydroxide solution, $NaHCO_3$, $Na_2CO_3$, alkoxides etc. (alkaline lactonization). Also, the autocatalytic conversion of KGA to ascorbic acid is described. The product of the lactonization reaction formed is crude ascorbic acid having a greater or lesser KGA content, from which ascorbic acid is then purified.

Ascorbic acid and KGA differ in their chemical structure essentially only by the lactone structure of ascorbic acid formed during the lactonization. Therefore, they resemble each other in their chemical reaction properties and have similar physical properties. Thus both acids, under the conventional processing preparation and purification conditions, exhibit pH- and temperature-dependent trends to decomposition and formation of colored minor components. The solubility of KGA and ascorbic acid is influenced by the four hydrophilic hydroxyl groups and the acid group. Both have a similar solubility product: they are highly soluble in polar solvents, in particular water, but are only sparingly soluble in nonpolar organic media.

Economic separation of a mixture of ascorbic acid and KGA is therefore difficult. This is evident, in particular, with the process steps described in the prior art of ascorbic acid preparation for separating the ascorbic acid from the unreacted starting material KGA or its derivatives.

According to JP 85019285, ascorbic acid and KGA can be separated from one another from aqueous solution by crystallizing the KGA as Na-KGA. Na-KGA must be converted back into free KGA in a subsequent step.

In alkali-catalyzed processes, the sodium salt of ascorbic acid is first produced, which must be converted in a further process step into the free AA, and is associated with an equimolar production of NaCl or $Na_2SO_4$. A further crystallization step is then generally necessary.

A process which produces free ascorbic acid without producing salt is described in U.S. Pat. No. 5,041,563. This proposes the base-catalyzed lactonization of a KGA ester with a long-chain amine in a dipolar solvent to give an ammonium ascorbate. The release of ascorbic acid is then induced by extracting the amine with a nonpolar solvent. Colored byproducts are also coextracted here.

Catalyst-free methods for synthesizing ascorbic acid from KGA esters have been known since approximately 1940. KGA esters are lactonized to ascorbic acid by simple heating in water, alcohols, or mixtures of water with a hydrophilic solvent at temperatures above 130° C. and residence times of from 30 minutes to 90 hours. Addition of citric acid and phosphate as buffer to set a constant pH is said to be able to increase the yields. A disadvantage here also is that the salts must then be removed again.

DE 861 841 describes a direct lactonization of a KGA ester with partial reaction and removal of ascorbic acid by selective crystallization and recycling of starting material. Unreacted starting material is removed by crystallizing the ascorbic acid.

The starting material, after the crystallization, must only be present at low concentration in the mother liquor, since otherwise the product is contaminated. Therefore operations must be carried out at high conversion rates.

U.S. Pat. No. 1,904,619 describes a process for continuous KGA (derivative) lactonization with partial conversion in aqueous solution. The product is isolated by crystallization and recrystallization from methanol. All mother liquors must be combined, concentrated and reconverted into an aqueous solution.

Hitherto, in the prior art, no economic process has been provided for separating ascorbic acid and KGA, so that generally in the reparation processes for ascorbic acid, the lactonization must be carried out under complete conversion of the KGA or the respective starting material in order to avoid contamination of the ascorbic acid with KGA. However, ascorbic acid preparation is distinguished by special requirements of purity and yield in all process stages: firstly, to enable the end product to be used in human nutrition, and secondly to decrease as far as possible the preparation costs.

In many processes the starting material or product is derivatized. Thus, in particular, the methyl or butyl esters of KGA are prepared which, in contrast to ascorbic acid, are soluble in alcohol. The separation processes described are, in particular due to the derivatization steps and the following liberation steps, highly complex, time-consuming, of low efficiency and, because of the high energy consumption and the use of organic, largely toxic solvents, are ecologically hazardous.

It is an object of the present invention, therefore, to provide an advantageous process to be able to separate ascorbic acid and 2-keto-L-gulonic acid economically, ecologically and efficiently from a polar, preferably aqueous, solvent. We have found that this object is achieved by the embodiments characterized in the claims of the present invention.

The present invention therefore relates to a process for removing ascorbic acid from a polar solvent 1 comprising ascorbic acid and 2-keto-L-gulonic acid, wherein the process comprises the following step:

(a) extracting the ascorbic acid from the solvent 1 with dialkylformamide (extraction medium 1), which has a miscibility gap with the solvent 1, in a liquid-liquid extraction.

In DE 38 31 071, KGA is extracted in the presence of from 2 to 6 molar equivalents of a long-chain amine at a $CO_2$ partial pressure of from 10 to 60 bar.

In EP 359 645, a dilute solution of KGA is extracted with an equal volume of a solution of an amine (Adogen 83) in kerosene, and back-extracted with nitric acid.

GB 1,426,018 describes the production of, inter alia, citric acid, lactic acid and oxalic acid from aqueous solutions by means of extraction On the basis thereof, EP 828 725 discloses a process for producing ascorbic acid by extracting the ascorbic acid with a water-immiscible composition which comprises (a), as primary extraction medium, at least one secondary or tertiary alkylamine in which the total number of carbons is at least 20, and (b) a polar extraction enhancer.

However, it has not been previously demonstrated that the two similar organic carboxylic acids ascorbic acid and KGA can be separated from one another by a liquid-liquid extraction.

Surprisingly, ascorbic acid can be selectively removed on an industrial scale in high purity from a polar solvent which comprises not only dissolved KGA but also ascorbic acid, by extraction with a dialkylformamide.

For the purposes of the invention, "extraction" means that, from a solid or liquid sample, the substances present therein are transferred using nonpolar to polar solvents or solvent mixtures into the respective extraction medium or extraction medium mixture. An extraction medium is also taken to mean a mixture of differing solvents, provided that the mixture has the properties described herein of the extraction medium.

For the purposes of the invention, a "liquid-liquid" extraction is an extraction of a substance dissolved in a liquid solvent by means of a second liquid solvent. The extraction conditions, for example the extraction medium or the temperature, can be selected in such a manner that a specific substance is essentially or preferentially extracted or not extracted.

Polar solvents, for the purposes of the invention, are aqueous solutions, including water, or polar aprotic or protic organic solvents, for example alkyl alcohols having an alkyl radical of from 1 to 4 carbons, for example methanol, ethanol, 1-propanol, 2-propanol, butanol, or, for example, acetone, acetonitrile, or dimethyl sulfoxide, or mixtures thereof.

A "polar phase" or a "polar extract" is taken to mean a phase or an extract which is obtained from an extraction using an above-described polar solvent or solvent mixture.

The term "aqueous solution" is taken to mean water or an aqueous solution, also, for example, deionized, demineralized, distilled or twice-distilled water. One or more substances can be dissolved in the aqueous solution or mixed therewith. Thus substances can be present which enhance the extraction, stability or solubility of the substances of value, or lead to preferred properties, for example pH, conductivity, salt concentration, etc., for example salt solutions or buffer solutions.

For the purposes of the invention, "extraction medium 1" is a solvent or solvent mixture which is immiscible with the solvent 1 and has a miscibility gap with the solvent 1. "Miscibility gap" means that ascorbic acid and/or KGA have a higher solubility in the extraction medium than in the solvent extracted.

Economic separation by extraction is possible when the distribution coefficients of the two substances to be separated, here ascorbic acid and KGA, are sufficiently different in an extraction medium. Owing to the structural similarity of ascorbic acid and KGA, this was not expected. This is also evident in the fact that, although the advantages of a partial autocatalytic lactonization, in particular the advantageous omission of catalysts, have been known since 1940, corresponding processes have not been used on an industrial scale owing to the absence of suitable separation processes for starting material and product.

The inventive extraction can be carried out as described in the documents cited herein or as in the examples, for example using a countercurrent flow extraction column or a mixer-settler cascade.

Preferably, in the inventive process, the extraction medium and the solvent are used in a ratio of from 1:1 to 5:1, preferably a ratio of from 2:1 to 3:1.

In a preferred embodiment, the extraction medium is an N,N-dialkylformamide having in each case N-bound C1 to C5 alkyl radicals. Particular preference is given to N,N-dibutylformamide (DBF) as extraction medium. Surprisingly, it has been found that, in particular using DBF, ascorbic acid can be selectively extracted from an aqueous KGA/ascorbic acid mixture.

According to the invention an economic separation of ascorbic acid from a mixture of ascorbic acid and KGA can be achieved when the ratio of the distribution coefficients under standard conditions for ascorbic acid to KGA is at least 1.5:1, preferably 4:1, more preferably 7:1 or greater, the distribution coefficient naturally being dependent on the temperature. The distribution coefficient can be determined by methods familiar to those skilled in the art, for example following a single-stage extraction by means of HPLC analysis and iodometric titration.

In a preferred embodiment, the inventive process uses no extraction enhancer in the liquid-liquid extraction.

Surprisingly, it has been found that in the inventive process for separating ascorbic acid and KGA, in contrast to the extraction process described in the prior art (EP 828 725), an extraction enhancer need not be used. EP 828 725 describes the extraction of ascorbic acid from an aqueous solution using a "first extraction medium", which consists of long-chain amines, and an extraction enhancer, which consists of a polar and protic extraction medium, the enhancer being a poorer extraction medium than the first extraction medium, and, in the extraction, a ratio of enhancer/first extraction medium of 2:1 being used. Preferred polar, in particular protic, enhancers are, according to EP 828 725, alkanols, ketones, aldehydes, esters and ethers of various molecular weights. For the purposes of the invention, the term "extraction enhancer" thus means the polar, in particular protic, extraction media disclosed in EP 828 725, in particular alkanols, ketones, aldehydes, esters and ethers of various molecular weights.

For the purposes of the invention, the term "no extraction enhancer" means that the ratio of an extraction enhancer to the "extraction medium 1" is from 0:1 to 1.9:1, preferably 1:1, more preferably 0.2:1, still more preferably 0.05:1. Most preferably, the fraction of the extraction enhancer is from 0% by volume to 1% by volume of the total volume of the extraction medium. In the inventive process, ascorbic acid and KGA can be separated without adding such an enhancer.

In a further preferred embodiment, in the inventive process the ascorbic acid is extracted from the solvent 1 using $C_1$ to $C_5$ N,N-dialkylformamide as extraction medium 1. Thus a phase 1 which comprises ascorbic-acid-loaded extraction medium 1, and a phase 2, which comprises the solvent 1 and KGA, is obtained. Preferably, the extraction medium is N,N-dibutylformamide (DBF).

As shown in the examples, DBF is suitable as extraction medium 1 for ascorbic acid from a mixture of ascorbic acid and KGA. Surprisingly, the ratio of the distribution coefficients of ascorbic acid and KGA in DBF is 7:1.

In an embodiment, in the inventive process solvent 1 is an aqueous solution, or a branched or unbranched $C_1$ to $C_4$ alkyl alcohol, preferably water or an aqueous solution. The term "aqueous solutions" comprises, according to the definition used herein, not only water but also buffers, fermentation solutions, salt solutions and other solutions which comprise substances for influencing, for example, the pH, the sterility of the solution or the stability of the substances. The solvent 1 can also be a fermentation broth or the supernatant of a decanted or filtered fermentation broth.

In a particularly preferred embodiment, in the inventive process solvent 1 is water or an aqueous solution, and extraction medium 1 is DBF.

Preferably, in the inventive process, the extraction is performed at a temperature from 10° C. to 60° C. Particularly preferably the temperature is from 15° C. to 30° C. Those skilled in the art, when selecting the preferred temperature, will balance the extraction efficiency against the refrigeration energy use to achieve the respective temperatures, and against the solubility of the starting materials at the respective extraction temperatures. For economic and ecological reasons, a temperature may be preferred which can be achieved without additional energy supply for cooling or heating (ambient temperature). To make possible efficient back-extraction, a higher temperature may be selected. Most preferably, the inventive process step is carried out at from 30° C. to 60° C., preferably at 40° C.

In a further embodiment, the inventive process comprises the following further step:
 (b) completely or partially back-extracting the ascorbic acid from the loaded extraction medium 1 using a polar extraction medium 2, an extraction medium 2 loaded with ascorbic acid being obtained.

"Completely or partially back-extracting", for the purposes of the present invention, means that ascorbic acid is essentially, preferably from 30% by weight to 100% by weight, back-extracted into the extraction medium 2. Preference is given to 50% by weight, more preference to 75% by weight or more.

To make efficient back-extraction possible, the concentration of ascorbic acid before the back-extraction in the extraction medium 2 is lower than in the extraction medium, that is to say preferably the content is 5% by weight, more preferably 1% by weight, or 0.1% by weight or less, most preferably 0% by weight.

The extraction medium 2 is a polar solvent as described above, preferably it is an aqueous solution or a branched or unbranched $C_1$ to $C_4$ alkyl alcohol.

Preferably, in the inventive process, the extraction medium 2 is used in a ratio of from 1:1 to 5:1 to the extraction medium 1, preference is given to a ratio of from 1:1 to 3:1.

In a preferred embodiment, the extraction medium 2 and the solvent 1 essentially consist of the same solvent components.

"Essentially consisting of the same solvent components" means here that the two agents are essentially identical and preferably differ in their solvent constituents by 30% or less, more preferably 10%, still more preferably 5% or less. Thus, for example, one medium can essentially consist of an aqueous solution having a low content of an alkyl alcohol, while the other medium consists of only an aqueous solution. In a preferred embodiment, the two media are identical with respect to their solvent components. Preferably, the extraction medium 2 is also polar. Particularly preferably, solvent 1 and extraction medium 2 are aqueous solutions.

In an embodiment, solvent 1 and extraction medium 2 consist of the same or similar solvents in which essentially the same substances are present except for the content of ascorbic acid and/or KGA.

"Essentially the same substances are present except for the content of ascorbic acid and/or KGA" means that the two media differ only in 30% of the dissolved and non-dissolved constituents except for ascorbic acid and KGA, more preferably 10%, still more preferably 5% or less.

In a preferred embodiment, in the inventive process the extraction temperature $T_1$ for the extraction of ascorbic acid from the solvent 1, which comprises a mixture of ascorbic acid and KGA, is lower than the back-extraction temperature $T_2$ for the back-extraction of ascorbic acid or KGA from the extraction medium using the extraction medium 2. Preference is given to a difference of more than from 5° C. to 100° C., more preferably more than 150° C., still more preferably 20° C.

As shown in GB 1,426,018, in the back-extract a high concentration can be achieved in back-extractions at higher temperatures than in the extraction using the same solvent, for example extraction at room temperature and back-extraction at 100° C., in particular a concentration which is similar to the starting concentration in the mixture.

Therefore, in one embodiment of the present invention, the extraction temperature is from 10° C. to 30° C. and that of the back-extraction is from 20° C. to 80° C. Preference is given to the combination of ambient temperature or room temperature, which here means a temperature of from 15° C. to 30° C., with a back-extraction temperature of from 40° C. to 60° C.

In one embodiment the inventive process also comprises the following further step:
 (c) recirculating the extraction medium 1 from which the ascorbic acid has been back-extracted as under step (b) to the extraction as under step (a).

Preferably, the extraction medium 1, before the recycling and reuse as extraction medium 1 in step (a), is partially or completely discharged, worked-up and only then recirculated. By means of the discharge, impurities are removed. The extraction medium can be purified, for example, by distillation, microfiltration or nanofiltration or adsorption (for example on activated carbon).

The content of material which is discharged is essentially dependent on the purity of the solvent 1 and the content of back-extracted valuable product, that is to say ascorbic acid, in the extraction medium after back-extraction has been completed. If the extraction medium 1, after the back-extraction with extraction medium 2, has only low contents of valuable product and a high content of impurities, a large fraction of extraction medium can be discharged. If the back-extraction is performed only partially, in the extraction medium there is still a high content of valuable product and those skilled in the art will routinely balance the loss due to discharge against the degree of contamination.

In one embodiment, the process comprises the step
 (d) concentrating the extraction medium 2 which is loaded with ascorbic acid;

and optionally the step
 (e) recirculating the extraction medium 2 vaporized in (d) (vapors) to the back-extraction as under step (b) as extraction medium 2.

"Concentration" means that the sample is reduced in volume and the concentration of the substance to be concentrated after it has been concentrated is higher than in the starting solution, but without precipitating out. Preferably, solvent is taken off or vaporized from the loaded extraction medium 2 up to the solubility limit of ascorbic acid. In a preferred embodiment exactly as much solvent is vaporized so that steady states can be established in the continuous plant with recycling. Preferably in step (d) the extraction medium is concentrated at from 30° C. to 50° C. to an ascorbic acid concentration of from 30 to 50% ascorbic acid.

Concentration can be performed, for example, by heating, in particular under reduced pressure, for example in a recirculating evaporator, thin-film evaporator etc. Samples may also be concentrated by dialysis. The concentration should occur under mild conditions, preferably at from −20° C. to 100° C., depending on reaction time, pressure and solvent. Preferably, the concentration is carried out at from 30° C. to 50° C., particularly preferably under reduced pressure. Depending on solvent or solvent mixture, the concentration can be carried out at atmospheric pressure (1013 mbar) to 10 mbar. In the case of aqueous solutions, they are preferably concentrated at from 500 mbar to 50 mbar. In a particularly preferred embodiment, a solution is concentrated at from 30° C. to 50° C., preferably at 40° C., and at from 50 mbar to 300 mbar, preferably at 70 mbar. Preferably, the concentrated solution, after each concentration by evaporation described herein, is cooled to ambient temperature or to from 20 to 25° C., for example by means of a heat exchanger.

The vaporized solvent (vapors) can then condense and be reused for the back-extraction in step (b).

In an embodiment, to recover the ascorbic acid, the ascorbic acid is isolated from the extraction medium 2 immediately, or after concentration and cooling of the solution.

The inventive process therefore also comprises, in a preferred embodiment, the following step:

(f) isolating, preferably crystallizing, ascorbic acid from the extraction medium 2 loaded with ascorbic acid, a mother liquor remaining.

Various process steps are known to those skilled in the art for recovering ascorbic acid from polar solvent. Thus, for example, evaporative, cooling or displacement crystallization steps, but also various drying processes, for example spray-drying for carboxylic acids, are described, in particular for ascorbic acid also. To isolate ascorbic acid, insoluble salts or derivatives can also be formed which then precipitate out in the solvent. Preferably, the ascorbic acid is isolated by evaporative, cooling or displacement crystallization. Particularly preferably, in the inventive process, ascorbic acid is precipitated out by cooling crystallization and isolated as solid.

The inventive process comprises, in an embodiment, the following further step:

(g) extracting ascorbic acid from the mother liquor remaining in the crystallization of the ascorbic acid as under step (f).

Preferably, for the back-extraction of the ascorbic acid from the mother liquor, the mother liquor is fed to the extraction as under step (a). Advantageously, the mother liquor is passed to the top (or last) stage of the first extraction column (or of a multistage extraction apparatus).

In a further embodiment, the KGA-loaded solvent 1 which remains after the extraction as under step (a) is recirculated to a process step for preparing ascorbic acid from KGA (step h) and mixed, for example, with new feed solution which is then fed to a lactonization reaction as described herein.

The product discharge of the lactonization reaction can then be subjected to the inventive process steps described herein for recovering ascorbic acid. Before extraction of the ascorbic acid as under step (a), in one embodiment, the product discharge of the lactonization reaction can be concentrated, for example as has been described above. After the concentration, advantageously, the solution is cooled and then the ascorbic acid is extracted according to the above-described steps.

Using the inventive process described herein, ascorbic acid could also be removed from a mixture of ascorbic acid and KGA, monoacetone-2-keto-L-gulonic acid and/or diacetoneketogulonic acid or other derivatives of ketogulonic acid.

The present invention, in one embodiment, also relates to a process for preparing ascorbic acid from 2-keto-L-gulonic acid which comprises the following steps:

(aa) partially lactonizing 2-keto-L-gulonic acid to ascorbic acid (ab) removing the ascorbic acid from the mixture with KGA by the inventive process.

The mixture of KGA and ascorbic acid can be prepared by processes known to those skilled in the art, for example by a process described herein for lactonizing KGA or its derivatives and if appropriate further reaction. Preferably, the mixture is prepared by direct partial lactonization, in particular by an autocatalytic lactonization of KGA to ascorbic acid.

"Partial lactonization" according to the invention means an incomplete conversion of the starting material to ascorbic acid. Preferably, in the inventive process, from 10% by weight to 95% by weight, more preferably from 20% by weight to 50% by weight, of the starting material are converted to ascorbic acid. Particular preference is given to an embodiment having a partial KGA conversion of from 20% by weight to 40% by weight.

The lactonization reaction (aa) can be carried out by processes as have been described in the prior art since 1933, provided that a mixture of the starting material, preferably KGA, and ascorbic acid is obtained in a polar solvent, preferably in an aqueous solution, in particular water. Because of the lack of separation processes, the literature generally describes complete conversions of KGA to ascorbic acid or combines, in the case of only partial conversion, the separation with the derivatization of KGA to an ester and subsequent crystallization of the ascorbic acid as described above.

Lactonization processes are described in the abovementioned prior art and the documents cited therein, which are here explicitly incorporated by reference into the subject matter of this description.

The process described herein could also serve for separating ascorbic acid from other starting products. Ascorbic acid is customarily prepared from 2-keto-L-gulonic acid, monoacetone-2-keto-L-gulonic acid or diacetoneketogulonic acid. Other starting materials, for example L-gulono-γ-lactone and the sodium salt of α-alkyl-KGA-pyranoside, have also been described.

Direct lactonizations are generally acid-catalyzed, preferably using hydrochloric acid as gas or using aqueous hydrochloric acid, and have long been known in the prior art.

DR 696 810 and DE 641 639 describe lactonization via the indirect route of formation of an ester of KGA or of diacetone-KGA-esters. The ester is soluble in alcohols, and AA is not, so that the AA precipitates out as solid. In addition, halogenated hydrocarbons can be supplied as precipitation aids.

In the case of alkali-catalyzed processes, the reaction rate of the lactonization is higher, which leads to higher space-time yields in the apparatuses. Base catalysts used, in addition to NaOH in various alcohol or alcohol/water mixtures, are alkali metal salts of weak acids (for example $NaHCO_3$ or sodium acetate), $Na_2CO_3$ or sodium methoxide in alcohols. In these processes, the sodium salt of ascorbic acid is first formed, which must be converted into free ascorbic acid in a further process step. A process for preparing free ascorbic acid is described in U.S. Pat. No. 5,041,563.

In the case of said acid processes, the catalyst must be removed. The acid can destroy the product. Under alkaline catalysis, an ascorbic acid salt is first prepared, which must be converted into free ascorbic acid.

From approximately 1940, the catalyst-free lactonization of KGA and KGA esters to give ascorbic acid by simple heating in water, alcohols or mixtures of water with a hydrophilic solvent at temperatures above 130° C. and residence times of 30 minutes to 90 hours has also been described. Addition of citric acid and phosphate as buffer to set a constant pH is said to be able to increase the yields.

DE 861 841 describes direct lactonization with partial conversion by heating a KGA ester in any water-containing, water-miscible organic solvent (alcohol/water or ether/water) and removal of product by selective crystallization and recycling of starting material. The starting material, however, after the crystallization, must only be present in low concentration in the mother liquor. U.S. Pat. No. 2,491,065 describes the autocatalytic direct lactonization of KGA or DAKA in aqueous solution at a KGA concentration <12% by weight, temperatures of 100-150° C. and residence times of from 20 minutes to 10 hours. U.S. Pat. No. 1,904,619 describes a process for continuous KGA (derivative) lactonization with partial conversion in aqueous solution, for example using an acidic ion exchanger as catalyst and recirculating unreacted KGA.

Advantageously, by means of the inventive process, a direct acid- or alkali-catalyzed or autocatalyzed partial lactonization can now be carried out, for example by means of an acidic ion exchanger (for example Bayer Levatit) or, preferably, by means of fixed-bed catalysis. Preferably, the lactonization is carried out at low temperatures which lead to low derivatization or decomposition of the resultant ascorbic acid, particularly preferably below 60° C., for example by means of biocatalysis or enzymic catalysis or in acid catalysis.

In a particularly preferred embodiment, in the inventive process the step (aa) for lactonizing the 2-keto-L-gulonic acid proceeds autocatalytically.

Lactonizations in most processes are carried out with complete conversion of the respective starting material. It is advantageous in the autocatalytic reaction that neither catalysts nor other aids are required and which must be removed from the reaction effluent. An economic use of the autocatalytic lactonization has failed previously owing to the fact that complete conversion proceeds inefficiently and with low yields. A suitable separation process for producing ascorbic acid from a mixture of KGA and ascorbic acid, as is obtained via partial conversion, has not been described and is made available in the present invention for the first time.

It is known that KGA in aqueous solutions can be lactonized by exposure to an aggravated temperature (T>25° C., T<200° C.) Preference is given to temperatures of from 40 to 180° C. Advantageously, a very short reaction time can thus be achieved in the reactor. If a solution of KGA in water is heated to 80-150° C. and the residence time in the reactor is kept at from 1 to 30 min, at KGA conversion rates around 25-30%, ascorbic acid selectivities around 90% can be achieved in solution. Partial conversion with recirculation of starting material has previously only been described for the case of KGA esters. Preferably, the initial concentration of KGA in water does not exceed 30%.

In a particularly preferred embodiment, a lactonization is carried out and then ascorbic acid is removed and the starting material, in particular KGA, is recirculated to the lactonization reaction.

The present invention therefore also relates to a process for preparing and recovering ascorbic acid, in which the step (aa) for lactonizing the 2-keto-L-gulonic acid is carried out autocatalytically with partial conversion under the following conditions:

| | |
|---|---|
| (aaa) | at a temperature from 60° C. to 180° C., preferably from 100° C. to 160° C.; |
| (bbb) | at an initial mass fraction of 2-keto-L-gulonic acid from 5% by weight to 50% by weight, preferably from 10% to 15%; |
| (ccc) | at a KGA conversion rate of from 10 to 40% by weight, preferably from 20 to 30% by weight; and/or |
| (ddd) | at a residence time in the lactonization reactor of from 1 to 30 min, preferably 10 min or less. |

Particular preference is given to an initial mass fraction of KGA of from 10 to 15% by weight, a reactor temperature of from 110° C. to 150° C. at a residence time of from 3 to 5 min and a KGA conversion rate of from 20 to 25% by weight.

Suitable reactors for the lactonization are, for example, tube bundle reactors, plate heat exchangers, helical tube reactors or jet reactors.

The reaction effluent from the lactonization reaction is concentrated in accordance with the concentration steps described above to achieve a steady-state operating condition. Then, in accordance with step (a), the ascorbic acid or KGA can be removed from the reaction effluent which is preferably cooled to ambient temperature or from 20° C. to 25° C.

Preferably, the reaction effluent, after the concentration, has a KGA content of from 5 to 30% by weight, particularly preferably from 8 to 25% by weight, and an ascorbic acid content of from 3 to 20% by weight, particularly preferably from 5 to 10% by weight.

In a preferred embodiment, in the inventive process the condensed vapors of the various evaporation steps substantially remain in the process and are used there as solvent, as has been described above for the various process steps. Particularly preferably, the respective solvents are vaporized above the respective operating pressure in such a manner that energy transfer from the vapor condenser to a first evaporation can take place to the evaporator of a second evaporation, in particular from the evaporation after the lactonization to the evaporation after the reextraction of ascorbic acid (step (d)).

According to the invention the individual steps of the process described herein can be carried out continuously or batchwise. A preferred embodiment is carrying out the steps continuously.

In an embodiment, the inventive process for recovering ascorbic acid or for preparing ascorbic acid comprises all herein-described steps (a) to (g) and/or (aa) to (cc) and/or (aaa) to (ccc). Advantageously, by this means ascorbic acid and/or KGA is obtained without producing salt.

The present invention is explained by the following examples, without these being restrictive in any way.

EXAMPLES

Example 1

Process

First, a mixture of solvent (LM) and KGA (for example an aqueous solution of a concentration of from 5 to 50% by mass, in particular 10-15%) is lactonized without further additive using a reactor which is indirectly or directly heated with steam or indirectly heated with another heat carrier (for example tube-bundle reactor, plate heat exchanger or jet reactor) with partial conversion at temperatures from 80° to 180° C., in particular at temperatures from 100 to 150° C., and residence times of 1-30 minutes, in particular from 1 to 10 minutes. In this case the KGA content is approximately 30% converted to AA with 90% selectivity. The reactor effluent is concentrated in an evaporator 2, for example in a recirculation evaporator, at relatively low temperatures (for example 40-80° C., and the corresponding vacuum), and then cooled in a heat exchanger 3 to approximately 25° C. The cooled and concentrated reactor effluent then typically has KGA concentrations of 5-25% (by mass) and AA concentrations of 1-10% (by mass). In the following process step, a multistage liquid-liquid extraction 4, the AA present in the reaction effluent is extracted using a suitable extraction medium (EM), for example N,N-dibutylformamide (DBF). In this case the EM is fed in countercurrent to the reactor effluent which is fed into the middle stage of the multistage apparatus. A small stream of LM is preferably fed to the last (or top) stage, also in countercurrent, of the multistage extraction apparatus. The mother liquor (ML) from the crystallization stage 8 is advantageously used for this. If the quantity of mother liquor is insufficient, in addition, condensed vapors from the evaporators 2 and 6 can be fed. The LM effluent of the multistage extraction apparatus 4, which in addition to the LM predominantly comprises KGA, is recirculated to the lactonization reactor 1. The multistage extraction apparatus can be, for example, a mixer-settler apparatus or an extraction column. The AA-loaded EM is substantially free from the AA in a second multistage extraction apparatus 5. The extraction medium, which is again passed in countercurrent flow, here can be the condensed vapors from the evaporators 2 and 6. The crude AA solution exiting is concentrated by evaporation to an AA concentration of approximately 45% (m/m) in the evaporator 6 (for example at approximately 40-60° C. and corresponding vacuum). The AA-depleted EM is recirculated to the first extraction apparatus 4. The crude AA solution is then cooled with cooling water in heat exchanger 7 and then fed to the crystallizer 8. The crude AA which has crystallized out is removed from the mother liquor (for example centrifuged off or removed using belt filters). The remaining mother liquor (ML, approximately 14% AA at 2° C. crystallization temperature) is recirculated as described above to the last (or top) stage of the first extraction apparatus 4. The amount of additional LM or condensed vapors is determined by the number of theoretical plates of the apparatus 4 and the KGA slip which can be tolerated. The lactonization reaction byproducts accumulate predominantly in the EM circuit, since the byproducts are more soluble in the somewhat non-polar EM phase than in the polar LM phase. To eject the high-boiling byproducts from the process, a substream of the EM is taken off, distilled and recirculated to the process. The bottoms product of the EM workup is fed to a residue incinerator or biological sewage treatment plant.

The condensed vapors from evaporators 2 and 6 remain in the process, apart from a small residue stream, and the process is therefore virtually free from waste water.

The energy released in the condensation of the vapors from the first evaporator 2 can substantially be used for the second evaporator 6 by generating a sufficient temperature difference between the evaporators via the choice of a suitable evaporator pressure.

Example 2

Laboratory System

A laboratory system was made up consisting of the above-described parts.

The system was operated as follows. An aqueous solution of KGA of a concentration of 9.83% by mass, at a mass flow rate of 198 g/h, and the recycle stream (bottom takeoff from the extraction column 4) were charged into the reactor 1. The reactor 1 was heated in this case to 160° C. The reactor was kept at a constant pressure of 10 bar by a pressurizing valve 6. The expanded reactor effluent had an AA concentration of 3.5% and a KGA concentration of 6.7%. It was transferred to the thin-film evaporator 2 and partially evaporated there at 50° C. and a pressure of 150 mbar. The concentrated reactor effluent comprised 5% AA and 9.43% KGA. The ascending vapors were condensed. From the condensate, sufficient was taken off (274 g/h) that the interfacial boundary between the aqueous phase and the organic phase stabilized in the upper part of the column 4, and the remainder was passed back as recycle to the evaporator circuit. The concentrated reactor effluent was transferred via a level controller of the thin-film evaporator, via the water-cooled heat exchanger 3 to the extraction column 4. The aqueous bottom takeoff of the column 4 was taken off at constant 618 g/h and recirculated to the reactor 1; it comprised 2.5% AA and 8.73% KGA. At the top end of the column internals, 95 g/h of deionized water were fed, and at the bottom end of the internals 600 g/h of water-saturated N,N-dibutylformamide were fed from extraction column 5. The regenerated extraction medium here still contained 0.58% AA. The overhead discharge of column 4 comprised approximately 3% AA. It was introduced at the bottom end of the internals of column 5. Here a mass flow rate of 619 g/h was established. At the top end of the column 5, 400 g/h of deionized water were fed. The aqueous bottoms discharge of column 5 was controlled in such a manner that the interface between the aqueous and organic phases stabilized in the upper part of the column. A takeoff stream of 416 g/h of crude product solution having an AA content of 2.9% and a KGA content of 0.47% was established. The overhead discharge of column 5 was, as described above, fed back to the column 4 at the bottom end of the column internals. Of the circulating extraction medium, at the top of column 5, approximately 10% of the recirculated stream was taken off as purge stream to discharge the byproducts. To maintain the mass flow rate of circulating extraction medium, fresh N,N-dibutylformamide was supplemented under level control. At the concentrations and mass flow rates specified, an AA yield of 68% results, which could be increased to 75% by improving the extraction or recirculating the crystallization mother liquor to column 4.

We claim:

1. A process for removing ascorbic acid from a mixture, the mixture comprising at least one polar solvent, ascorbic acid and 2-keto-L-gulonic acid (KGA), said process comprising:
   (a) selectively extracting the ascorbic acid from the mixture with dialkylformamide (extraction medium 1), the extraction medium 1 having a miscibility gap with the mixture, in a liquid-liquid extraction, and
   wherein, after extraction, an ascorbic-acid-loaded extraction medium 1 and a KGA-loaded mixture are obtained.

2. A process as claimed in claim 1, wherein the dialkylformamide is N,N-dibutylformamide.

3. A process as claimed in claim 1 further comprising:
   (b) back-extracting the ascorbic acid from the ascorbic-acid-loaded extraction medium 1 using a polar extraction medium 2, wherein an ascorbic-acid-loaded extraction medium 2 and an ascorbic-acid-depleted extraction medium 1 are obtained.

4. A process as claimed in claim 3, wherein the polar solvent and/or the extraction medium 2 is water or an aqueous solution.

5. A process as claimed in claim 3, wherein the extraction temperature of the step (a) $T_1$ is from 5° C. to 100° C. lower than the back-extraction temperature of the step (b) $T_2$.

6. A process as claimed in claim 3, further comprising:
(c) recirculating the ascorbic-acid-depleted extraction medium 1 from step (b) to the extraction as under step (a).

7. A process as claimed in claim 3, further comprising:
(d) concentrating the ascorbic-acid-loaded extraction medium 2; and
(e) optionally, recirculating the extraction medium 2 vaporized in (d) (vapors) to the back-extraction as under step (b) as extraction medium 2.

8. A process as claimed in claim 3, further comprising:
(f) isolating ascorbic acid from the ascorbic-acid-loaded extraction medium 2, a mother liquor remaining.

9. A process as claimed in claim 8 further comprising:
(g) extracting ascorbic acid from the mother liquor remaining in a crystallization of the ascorbic acid as under step (f).

10. A process as claimed in claim 9, wherein, for the extraction of the ascorbic acid from the mother liquor, the mother liquor is fed to the extraction as under step (a).

11. A process as claimed in claim 1, wherein the KGA-loaded mixture from the extraction as under step (a) is recirculated to a process for preparing ascorbic acid from KGA.

\* \* \* \* \*